(12) United States Patent
Chen et al.

(10) Patent No.: US 9,610,413 B2
(45) Date of Patent: Apr. 4, 2017

(54) POWDER MEDICAMENT MOUTHPIECE AND APPLICATION

(75) Inventors: Qingtang Chen, Zhejiang (CN); Xin Chen, Jiangsu (CN)

(73) Assignee: Leqing Kanghua Medical Supplies Co., Ltd., New York, NY (US)

( * ) Notice: Subject to any disclaimer, the term of this patent is extended or adjusted under 35 U.S.C. 154(b) by 635 days.

(21) Appl. No.: 13/994,759

(22) PCT Filed: Dec. 15, 2011

(86) PCT No.: PCT/CN2011/084070
§ 371 (c)(1),
(2), (4) Date: Sep. 2, 2013

(87) PCT Pub. No.: WO2012/079524
PCT Pub. Date: Jun. 21, 2012

(65) Prior Publication Data
US 2013/0333699 A1    Dec. 19, 2013

(30) Foreign Application Priority Data
Dec. 17, 2010 (CN) .......................... 2010 1 0596111

(51) Int. Cl.
*A61M 15/00* (2006.01)
*A61M 15/06* (2006.01)
*A61M 11/00* (2006.01)

(52) U.S. Cl.
CPC .......... *A61M 15/00* (2013.01); *A61M 11/003* (2014.02); *A61M 15/0028* (2013.01); *A61M 15/06* (2013.01); *A61M 15/0021* (2014.02); *A61M 15/0086* (2013.01); *A61M 2202/064* (2013.01); *A61M 2205/75* (2013.01)

(58) Field of Classification Search
CPC .. A61M 15/00; A61M 15/06; A61M 15/0028; A61M 15/0021; A61M 15/0086; A61M 11/003; A61M 2205/75; A61M 2202/064; F16L 33/2076; F16L 55/0331; F16L 21/007; F16L 21/08; F16L 37/02; F16L 37/04; G01N 30/6034; B07B 9/00; A41D 13/1138
USPC ........... 128/203.15; 55/341.2, 380, 474, 482, 55/486, 489; 96/362, 363, 368; 285/913, 285/345, 399, 330
See application file for complete search history.

(56) References Cited

U.S. PATENT DOCUMENTS

| | | | | |
|---|---|---|---|---|
| 5,287,850 A | * | 2/1994 | Haber ............... | A61M 15/0091 128/203.15 |
| 5,765,552 A | * | 6/1998 | Zanen ............... | A61M 15/0065 128/203.12 |

(Continued)

FOREIGN PATENT DOCUMENTS

GB    WO 02089875 A1 * 11/2002   ........ A61M 15/0065

*Primary Examiner* — Peter S Vasat
*Assistant Examiner* — Margaret Luarca
(74) *Attorney, Agent, or Firm* — Bei & Ocean; George G. Wang

(57) ABSTRACT

A powder medicament mouthpiece comprising at least one section of through suction tube (1) and a filter (2). One end of the suction tube is a medicament inlet, and the other end (16*a*) is a suction outlet. The filter (2) is arranged within the suction tube (1). The powder medicament mouthpiece can be connected to multiple models of dry powder inhalers to separate powder medicament from dry powder, and allows for significantly improved efficacy.

3 Claims, 4 Drawing Sheets

(56) References Cited

U.S. PATENT DOCUMENTS

| | | | | |
|---|---|---|---|---|
| 6,036,126 A | * | 3/2000 | Cappola | B07B 1/28 209/315 |
| 7,237,550 B1 | * | 7/2007 | Lin | A62B 18/025 128/205.27 |
| 7,360,537 B2 | * | 4/2008 | Snyder | A61M 15/0086 128/200.23 |
| 2002/0121275 A1 | * | 9/2002 | Johnson | A61M 15/0086 128/200.22 |
| 2002/0121277 A1 | * | 9/2002 | Pera | A61M 15/0028 128/203.15 |
| 2005/0039744 A1 | * | 2/2005 | Szirmai | A61M 15/02 128/203.15 |
| 2007/0175476 A1 | * | 8/2007 | Lipowicz | A61M 15/06 128/205.29 |
| 2009/0229609 A1 | * | 9/2009 | Carrier | A61M 15/0021 128/204.15 |
| 2010/0078020 A1 | * | 4/2010 | Hyde | A61M 15/02 128/203.14 |

* cited by examiner

POWDER MEDICAMENT MOUTHPIECE AND APPLICATION

FIELD OF THE INVENTION

This invention relates to a medical apparatus, especially a powder medicament mouthpiece and its application, specifically, a device for either standalone use or for use in conjunction with various models of dry powder inhalers.

BACKGROUND OF THE INVENTION

Presently, there are a number of models of dry powder inhalers being used to treat asthma, but the curing rate by the GINA standard is only about 5%. The powder medicament particles for inhalation can easily agglomerate and are difficult to separate. The dosage is low and thus packaging is difficult. Therefore, it is usually mixed with a large amount of lactose, as high as 98.8% of the total volume of dry powder. However, long-term inhalation of lactose can produce side effects. If the amount of the lactose inhalation is to be reduced, the dosage of dry powder has to be reduced, which reduces the efficacy of treatment as well.

SUMMARY OF THE INVENTION

An object of the present invention is to provide a mouthpiece to filter out the powder medicament, for significantly improved efficacy.

Technical Solution

The object of the invention is realized in the following way: a powder medicament mouthpiece comprising a suction tube (1) and a filter (2), characterized in that it comprises at least one section of a pass-through suction tube (1), which has a medicament inlet at one end and a suction outlet (16a) at another end, and the filter (2) is disposed within the suction tube (1).

In this invention, suction tube (1) is connected subsequently with at least one section of suction tube, the filter (2) in the suction outlet formed by them is a filter cup, or is comprised of filtering silk, net, cloth, membrane or bag, or the filter (2) is located at any portion through the whole suction outlet, or one or more filter (2) of the same size can be mounted at different locations, or one or more filter (2) of different sizes can be mounted.

In this invention, the filter (2) is comprised of at least two layers of hollow cups. The slightly larger hollow cup (a) covers outside the slightly smaller hollow cup (b) of the identical shape, with the concave point (91) of one cup mouth fit with the convex point (92) of the other, to lock the overlapped cups, so that some hollowed parts (93) of one cup are staggered with those of the other (94), having a pass-through gap in the overlap of the two cups. If, for example, the gap between overlapped the cup is 10 μm, particles with the size less than 10 μm would be able to pass through the gap. To avoid contamination of filter cups when contacted by the hand, the external surface of the outer cup is not pass-through, while there are a number of grooves on the inner wall of it leading to the hollowed part at the bottom (96).

In this invention, a filter bag is placed inside the filter cup (a), with a support frame placed inside the bag to hook on or fix the bag mouth, or the mouth of the support frame and cup (a) mouth can be separably buckled together.

In this invention, the number, shape, size, layers of the filtering pores of the filter (2) can be predetermined as required. For example, it can be set to allow passage of powder medicament with the size below 5 μm while stopping the excipient sized over 6 μm.

In this invention, the powder medicament mouthpiece is used by connecting it to, respectively, different models of dry powder inhalers, or connecting at least two said powder medicament mouthpieces respectively in parallel with multiple models of dry powder inhalers.

In this invention, the powder medicament mouthpiece is applied to a number of models of dry powder inhalers, which include a dry powder inhaler, powder medicament mouthpiece box, accuhaler, turbuhaler and the inhaler covered by Chinese patent No. ZL2005100 38681.1.

In this invention, between the suction tube (1) and inhaler dry powder suction outlet is provided with a connection base (3), consisting of central tube body and connector (5), the central tube body (31) is inserted into the inhaler dry powder suction outlet, the embossments (32 and 33) on the central tube body (31) hook on the inner wall of the dry powder suction outlet, the connector (5) is connected with suction tube (1), or is connected in parallel with at least two suction tubes (1).

In this invention, the butt joint inner tube (8) is a hollow tube, with a thin front end and a horn-shaped rear end, a ball (8a) can be provided inside the horn cavity, a fence (8b) to stop the ball is provided at the end of the horn cavity, the front end of the butt joint inner tube (8) can be inserted directly into the dry powder suction outlet of the dry powder inhaler, or into the central tube body (31) of the connection base (3).

In this invention, the connection base (3) is first plugged into inhaler dry powder suction outlet, then the butt joint inner tube (8) is plugged into central tube body (31) by aligning the embossment (8d) on the butt joint inner tube (8) with the notch (5a) on the connection base, to lock the direction, so that the front arc of the butt joint inner tube (8) just matches with the arc inside the connected inhaler dry powder suction outlet, to reduce air leakage and facilitate suction out of powder medicament in the first time.

Beneficial Results

The advantages of this invention are: the powder medicament mouthpiece is connected with multiple models of dry powder inhalers, to make use of their advantages for significant efficacy.

BRIEF DESCRIPTION OF THE DRAWINGS

FIG. 8 is the connection schematic diagram of mouthpiece and the outer sleeve tube (111), connection base (3) with the accuhaler (W3) in this invention.

DETAILED DESCRIPTION OF PARTICULAR EMBODIMENTS OF THE INVENTION

In the following, this invention is further described in conjunction with attached drawings and embodiments.

Embodiment 1

Figure 1:
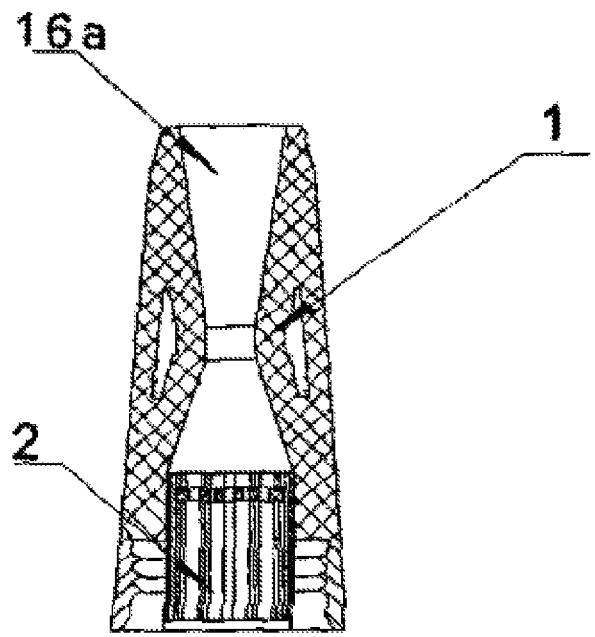
FIG. 1 is the sectional schematic diagram of the suction tube (1) and filter (2) of this invention.
Figure 2:
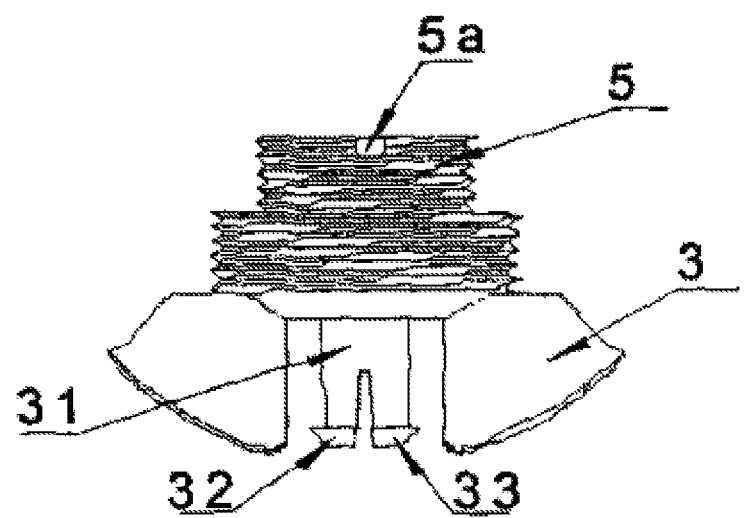
FIG. 2 is the external schematic diagram of the connection base (3) of this invention.
Figure 3:
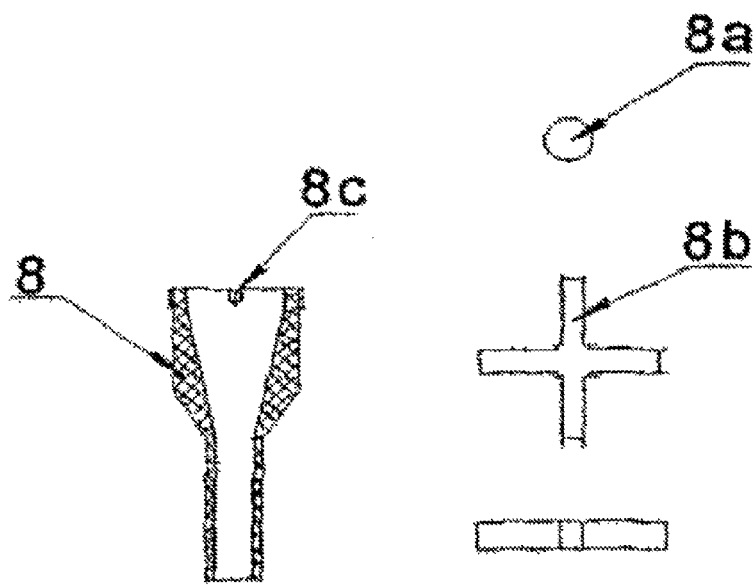
FIG. 3 is the sectional schematic diagram of the butt joint inner tube (8), ball (8a) and fence (8b) of this invention.
Figure 4:
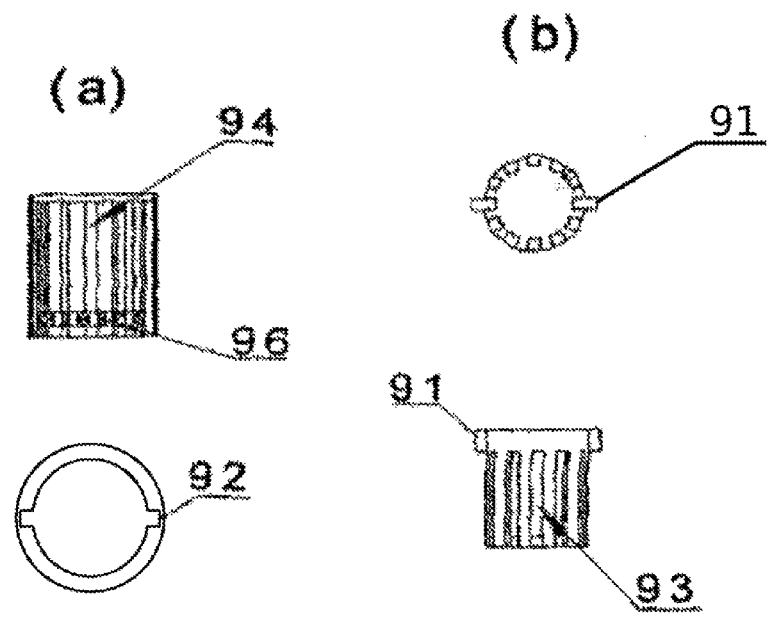
FIG. 4 is the schematic diagrams of the filter (2) of this invention: (a) outer hollow cup, and (b) inner hollow cup.

Powder medicament mouthpiece (FIG. 1). Put suction tube (1) into the filter (2) with the inlet upward, pour the powder medicament into the inlet, then tilt and put the suction outlet (16*a*) of suction tube (1) into the mouth to suck the powder medicament. If the suction tube (1) is made by bending the inlet upward, it can facilitate pouring the powder medicament into it and it cannot easily go out. The inhaling rate can be increased by extending one end of the suction outlet (16*a*) by about 8 cm. The suction outlet (16*a*) with two outlets can be used by nose. After use, dismantle and clean the inhaler, and dry it up for later use.

Embodiment 2

Figure 5:
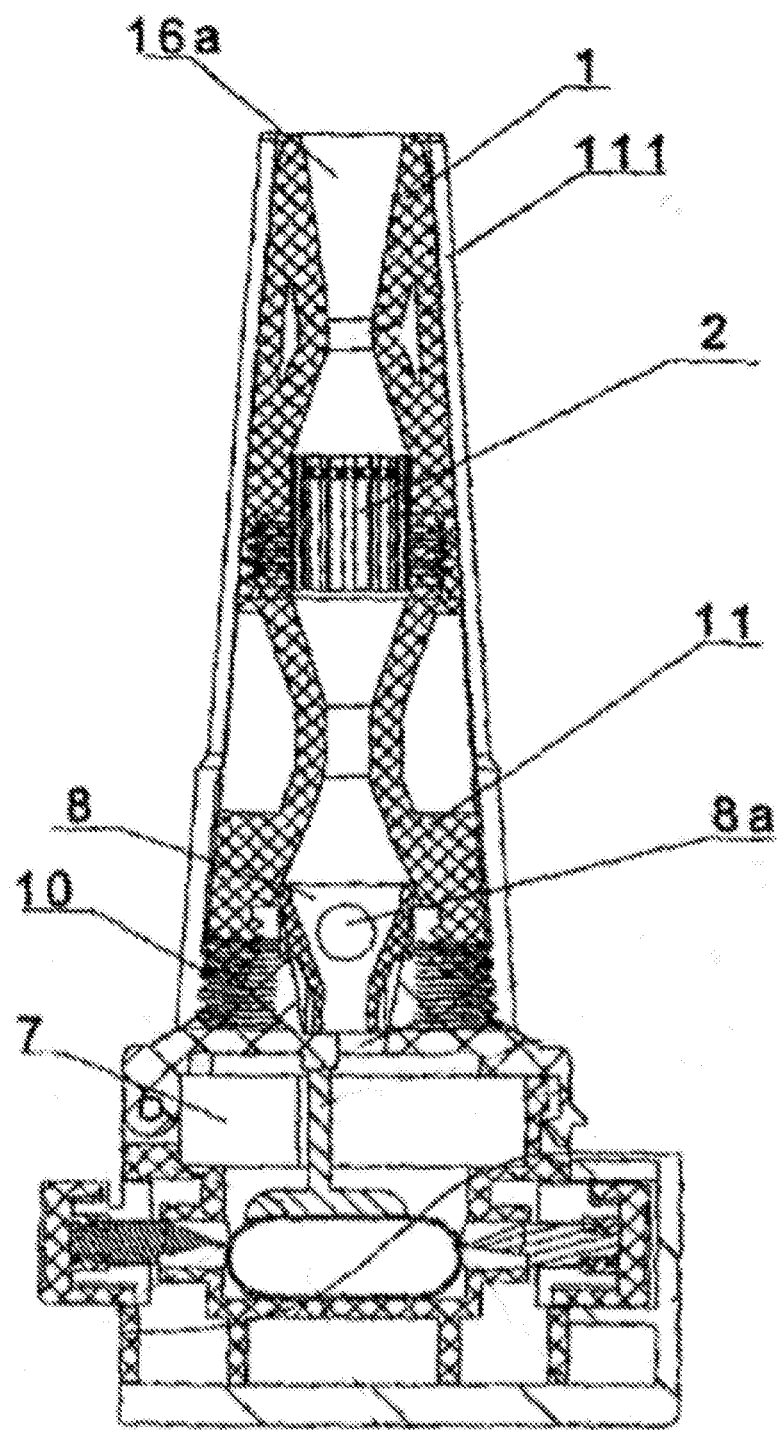
FIG. 5 is the sectional schematic diagram of connection of the mouthpiece of this invention consisting of suction tubes (1) and (11) and the outer sleeve tube (111) with the dry powder inhaler.
Figure 6:
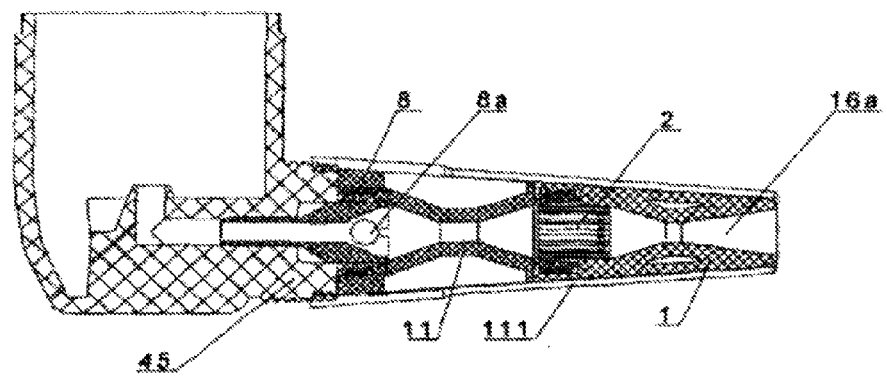
FIG. 6 is the connection schematic diagram of the mouthpiece of this invention with the embossment (45) on one side at the bottom of powder medicament mouthpiece box.
Figure 7:
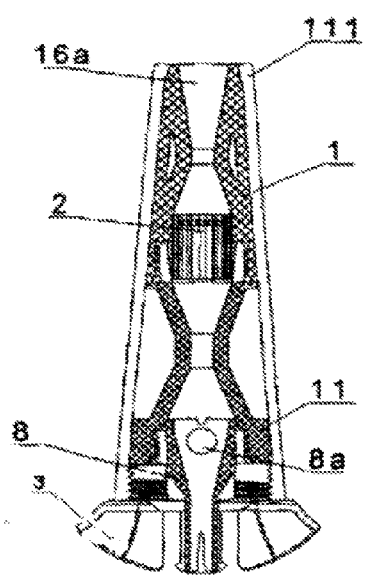
FIG. 7 is the connection schematic diagram of suction tubes (1) and (11) and the outer sleeve tube (111) with the connection base (3) in this invention.
Figure 3:
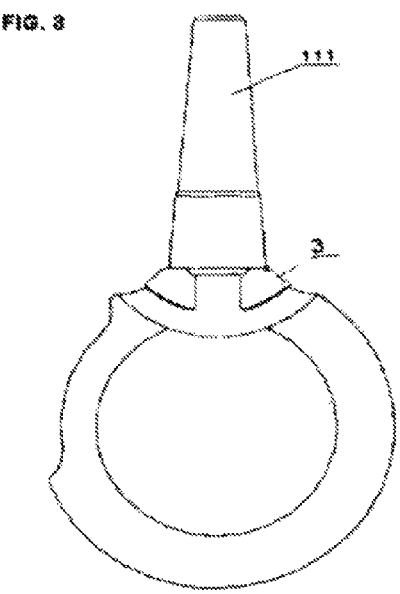

Connection of powder medicament mouthpiece with powder medicament inhaler (FIG. 5). First, put the filter cup into the cavity of suction tube (1), and connect suction tube (11) with suction tube (1) to form the mouthpiece. Put the ball (8*a*) into the butt joint inner tube (8), and fix the fence (8*b*) at the horn mouth; plug the butt joint inner tube (8) into the suction outlet (19*a*) of the filtered powder medicament inhaler, connect the mouthpiece with the connection (10) of filtered powder medicament inhaler, and then cover the mouthpiece with outer sleeve tube (111), and connect it with the connection (10) to form a new powder medicament inhaler. Then open the inhaler upper base, put the inhaling capsule into the capsule chamber, and pierce the capsule with the press pin. During suction at the suction outlet (16*a*), the ball (8*a*) vibrates, to collide the excipient to separate from the powder medicament, and the excipient is stopped in the filter (2), while the filtered out powder medicament is quickly inhaled into the respiratory tract. In case of.

Embodiment 3

First, rotate Seretide (W3) to the suction mode, to expose the powder medicament suction outlet, plug the central tube body (31) on connection base (3) into the powder medicament suction outlet, then plug butt joint inner tube (8) into central tube body (31) by aligning the embossment (8*d*) on it with the notch on connection base (3), connect the mouthpiece with the connector (5) on connection base (3), and finally put on the mouthpiece sleeve (111) for inhalation (FIGS. 7 and 8).

In the embodiments, the parts of this invention can be made by injection moulding or with metal and new materials. And the finished parts can be fitted and connected.

What is claimed is:

1. A powder medicament mouthpiece, comprising a suction tube and a filter, the suction tube having at least one through section, a first end of the suction tube configured as a medicament inlet, and a second end configured as a suction outlet, the filter being arranged within the suction tube and comprising a filtering pore or gap with a size greater than the size of a medicament particle and smaller than the size of an excipient particle, wherein the filter comprises an outer cup and an inner cup, the inner cup being nested within the outer cup, the inner cup having a sidewall with a plurality openings therethrough, and the outer cup having a sidewall with a plurality of openings therethrough; the openings of the inner cup sidewall are aligned away from the openings of the outer cup sidewall to prevent a direct flow from the openings of the inner cup sidewall to the openings of outer cup sidewalls; a gap between the inner sidewall and the outer sidewall to allow a flow from the openings of the inner cup sidewall via the gap to the openings of the outer cup sidewall; and the gap serves as the filtering gap and is sized to allow a medicament particle to pass through while preventing passage of an excipient particle.

2. The powder medicament mouthpiece of claim 1, wherein a butt joint inner tube is further provided, which is extended into inside the outlet of the inhaler or inside the central tube of the connection base.

3. The powder medicament mouthpiece of claim 2 wherein the butt joint inner tube has an arc-shaped front end matching an arc-shaped inside of the outlet of the inhaler for reducing air leakage when the butt joint inner tube is connected to the outlet of the inhaler.

* * * * *